United States Patent [19]
Wulfsberg

[11] Patent Number: 5,718,663
[45] Date of Patent: Feb. 17, 1998

[54] ENDOSCOPE OPTICAL SYSTEM WITH A WINDOW PLATE HAVING A LIGHT SCREEN

[75] Inventor: Jens Peter Wulfsberg, Ammersbek, Germany

[73] Assignee: Olympus Winter & Ibe GmbH, Hamburg, Germany

[21] Appl. No.: 666,753

[22] Filed: Jun. 19, 1996

[30] Foreign Application Priority Data

Jul. 17, 1995 [DE] Germany .................. 195 25 995.5

[51] Int. Cl.$^6$ .................................................. A61B 1/06
[52] U.S. Cl. .................................... 600/176; 600/160
[58] Field of Search ........................... 359/642, 707, 359/724; 600/160, 175–177, 181

[56] References Cited

U.S. PATENT DOCUMENTS

| | | | |
|---|---|---|---|
| 4,111,561 | 9/1978 | Plummer | 356/225 |
| 4,421,386 | 12/1983 | Podgorski | 359/894 |
| 4,500,181 | 2/1985 | Takahashi | 600/177 X |
| 4,772,094 | 9/1988 | Sheiman | 359/466 |
| 4,942,867 | 7/1990 | Takahashi et al. | 600/176 X |
| 5,193,525 | 3/1993 | Silverstein et al. | 600/125 |
| 5,448,990 | 9/1995 | De Faria-Correa | 600/177 X |

*Primary Examiner*—Richard J. Apley
*Assistant Examiner*—John P. Leubecker
*Attorney, Agent, or Firm*—Walter C. Farley

[57] ABSTRACT

An endoscope optical system has a shaft containing parallel image and light guides, the distal ends of which are covered by a window which closes the distal end of the shaft and which has a light screen near the separating line between the cross-sectional regions of the image guide and the light guide. The window is a one-piece window plate with at least one circular slot forming a light screen. The slot extends parallel to the separating line and is formed in one of the inner or outer surfaces of the window plate. Multiple slots forming a labyrinth are also disclosed.

7 Claims, 3 Drawing Sheets

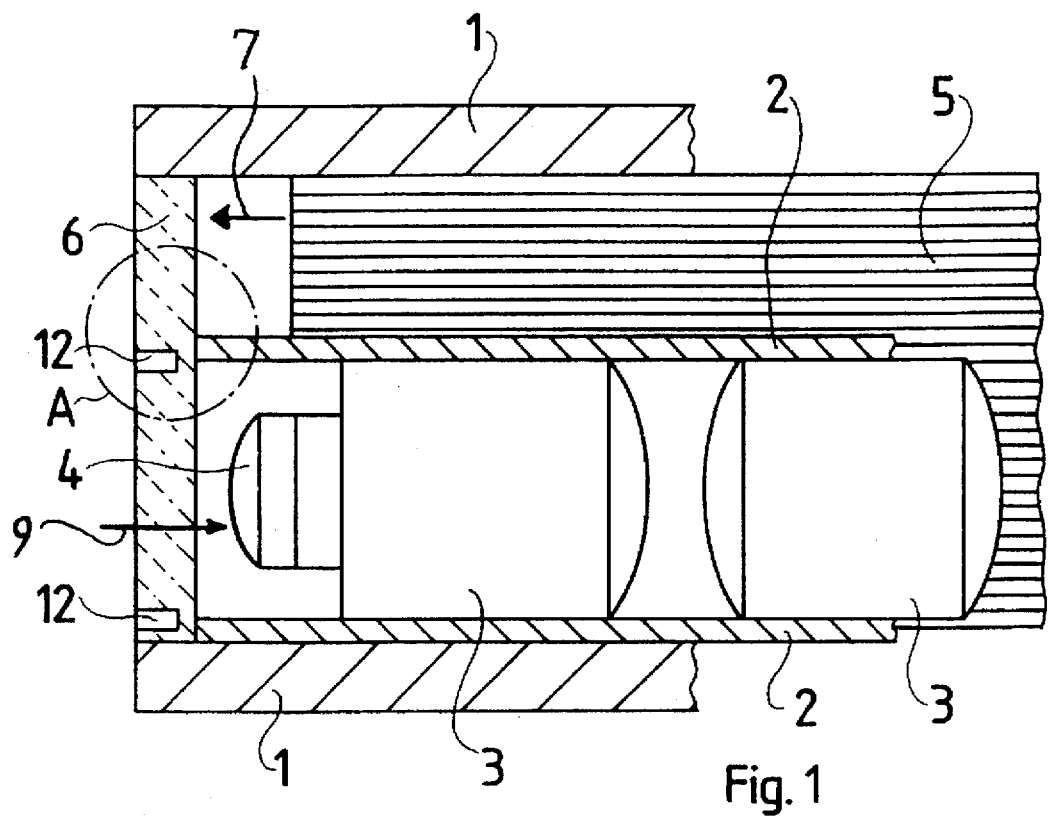
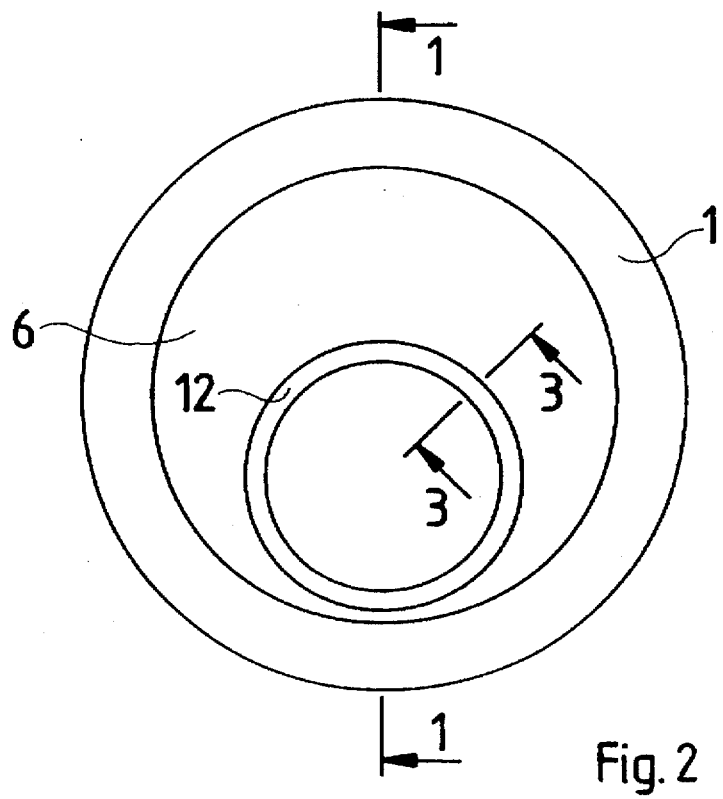

ENDOSCOPE OPTICAL SYSTEM WITH A WINDOW PLATE HAVING A LIGHT SCREEN

FIELD OF THE INVENTION

The invention relates to an endoscope optical system having a shaft containing parallel image and light guides, a window covering the distal end of the shaft, and a light screen to diminish stray light transmission from the light guide to the image guide.

BACKGROUND OF THE INVENTION

Optical systems are generally used as inserts in endoscopic instruments, predominantly for medical use, and have an image guide and a light guide in a shaft, the image guide being used for viewing, that is to say receiving light from the viewing location with a distally disposed objective, while the light guide, arranged parallel and next to the image guide, radiates light forwardly (distally) onto the viewing location.

The optical system can be of flexible or rigid construction. The image guide is conventionally constructed in a rigid system as a rod lens arrangement. The light guide is conventionally always constructed as a bundle of light-transmitting fibers.

Protecting the image guide and the light guide from media, particularly water which penetrates from the exterior, is always problematic with such endoscope optical systems. Particularly with medical optical systems, which are sterilized with hot steam, major sealing problems arise in this connection.

The sealing problem may be best solved at the distal end of the shaft by a window which is fastened within the shaft in a sealed manner to close it and cover the image guide and the light guide.

However, problems arise with the transmission of light from the light guide into the image guide by reflection in the window. This can be referred to as "stray" light.

A construction is known from DE 3708124 A1 (FIG. 1) in which only the image guide is covered with a window. Transmission problems are thereby avoided. However, the sealing of the instrument, particularly of the light guide, is unsatisfactory. FIG. 16 shows a construction in which the light guide and image guide are covered with separately mounted windows. The mounting between the windows constitutes a light screen which impedes the transmission of light from the light guide to the image guide. However, this arrangement is difficult to construct particularly as to the sealing problems.

An endoscope optical system is known from DE 9016829 U1 with a one-piece continuous window plate which covers not only the image guide but also the light guide. There is no provision to prevent the transmission of stray light.

A construction of this general type is known from DE 4211547 A1 in which the light guide and image guide are covered by a common window which is, however, composed of many parts, the adjoining edges of the parts of this window being provided with a blackening or vapor deposited layer as a light screen. Light transmission is prevented in this case. However, there are considerable sealing and strength problems with a composite glass plate.

A construction is also known from DE 3923007 C2 (similar structures in JP 6-23811 B2 and JP 2-132409 A) in which a window is provided in the form of a window plate which covers the entire shaft in one piece, that is to say not only the light guide but also the image guide, and which has no light screen in the region of the separating line between the image guide and light guide. Thus, the window is completely translucent but has a light trap at that point due to a wedge-shaped structure. One of the two surfaces of the plate can optionally (FIGS. 7 and 8) be of reflection-reducing construction in a suitable manner. The stable, one-piece construction of the window plate, with which the sealing problems may be solved extremely well, is advantageous in this connection. However, the expensive, wedge-shaped construction of the window plate and, in particular, the necessary large breadth of the light trap are disadvantageous in this construction. The image guide and light guide must be separated by a relatively large spacing which results in an undesired increase in the diameter of the endoscope optical system.

This publication also discloses (FIG. 8) the possibility of providing one of the surfaces of the window plate with grooves. However, these are of very shallow construction and merely serve to make the surface of the light trap reflection-reducing with the application of many grooves over a large area in the manner of knurling.

SUMMARY OF THE INVENTION

An object of the present invention is to provide an endoscope optical system which ensures lasting sealing of the interior of the endoscope optical system with effective prevention of reflection of light from the light guide into the image guide and with a compact cross-sectional construction.

Briefly described, the invention comprises an endoscope optical system with a generally tubular shaft, an image guide in the shaft and a light guide parallel with the image guide in the shaft, each of the shaft and guides having a distal end, the image and light guides being separated from each other along a separating line. A one-piece window is mounted at the distal ends of said shaft and the image and light guides and closes said distal end of said shaft. The window has substantially parallel inner and outer surfaces, and at least one slot extending into the window from at least one of the inner and outer surfaces, the slot being aligned with the separating line and forming a light screen to diminish transmission of stray light from the light guide to the image guide.

The window plate is one-piece construction in accordance with the invention, i.e., it is connected in a sealed manner to the shaft of the endoscope optical system only at its edge, which results without problems in a long lasting, good seal of the interior of the endoscope optical system from ambient conditions. The light screen is constructed in the form of one or a few slots which are formed in the surfaces of the window plate and which extend like transverse walls transversely to the disruptive light beams which, when reflected from the light guide into the image guide, extend within the light plate substantially transversely to the axis of the shaft of the endoscope optical system. Transverse reflection in the window plate is thereby substantially reduced, the slot depth determining the degree to which reflection is suppressed, balanced against the remaining mechanical strength of the window plate.

A plurality of slots can be advantageously provided, particularly two slots which make more effective screening of the reflected light possible, even with a smaller depth which impairs the mechanical stability of the window plate to a lesser extent.

A particularly effective prevention of transverse reflection may be achieved by forming the slots in different surfaces of the window plate, and also the slots advantageously are provided in a labyrinthine arrangement.

The light reflected transversely through the window plate from the light guide to the image guide may be particularly effectively prevented from transmitting across in this manner with a suitable arrangement of angled side walls of the slots.

By forming the slot base with slanted surfaces, due to reflection back of the light beams at the oblique surfaces of the slot base, the light can be prevented from transferring over into the region of the image guide in this manner at that point also.

BRIEF DESCRIPTION OF THE DRAWINGS

The invention is illustrated schematically and by way of example in the accompanying drawings wherein:

FIG. 1 is a side elevation, in longitudinal section along line 1—1 of FIG. 2, of the distal end region of a first embodiment of an endoscope optical system in accordance with the invention;

FIG. 2 is a distal end view in the axial direction of the embodiment of FIG. 1;

DESCRIPTION OF THE PREFERRED EMBODIMENTS

Figure 3:
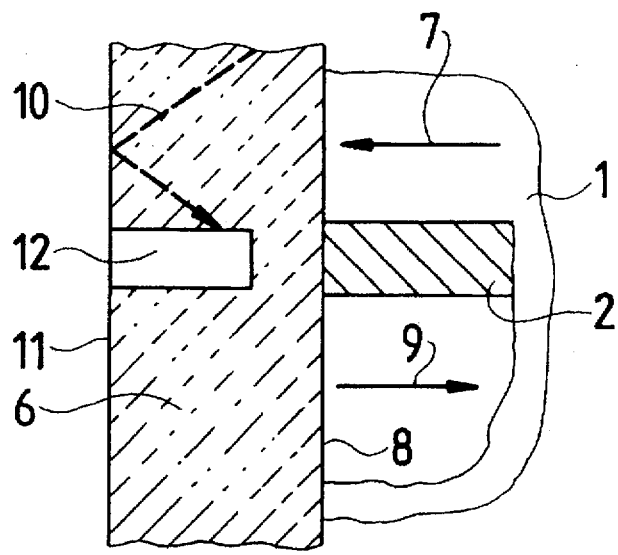
FIG. 3 is an enlarged sectional view through the window plate along line 3—3 of FIG. 2 in the region A of FIG. 1.

FIG. 1 is a sectional view of the distal end region of a rigid endoscope optical system, as is commonly used for medical purposes. The optical system is surrounded by a shaft 1 constructed as a round tube. An image guide tube 2 is arranged eccentrically within shaft 1, the guide tube containing an image guide in the form of a stack of lenses constituted by rod lenses 3. Cemented onto the distally frontmost rod lens 3 is an objective lens 4.

A crescent-shaped cross-sectional region, in this conventional arrangement, surrounds the image guide tube within the shaft 1 and is completely filled with a light guide 5 which comprises a bundle of parallel light-guiding fibers. The distal end surface of light guide 5 is ground flat.

The distal opening of shaft 1 is closed by a window plate 6 whose edge is fastened to the inner wall of the shaft 1 in a liquid and gas-tight manner by suitable means, for instance, by soldering or by means of an internally and externally soldered window support, not shown.

As is shown by the highly schematic enlarged sectional view of FIG. 3 through the window plate in the region of the separating line between the cross-sectional region of light guide 5 and of the image guide situated within light guide tube 2, light shines out of the light guide in the direction of arrow 7 onto an inner surface 8 of window plate 6. Light coming through the window plate in the direction of arrow 9 in the region of the image guide is intercepted by the objective lens 4 of the image guide.

The light guiding fibers constituting image guide 5 radiate light at their end surfaces not only parallel with the direction of the arrow 7 but also at oblique angles. This stray light can, as shown by dashed-line arrow 10, be reflected at the outer surface of window plate 6 and can pass beyond the partition wall formed by image guide tube 2 into the region of the image guide and onto the objective lens 4, possibly after zig-zag multiple reflection at inner surface 8 and outer surface 11 of window plate 6. These extremely disruptive light reflections are to be avoided.

For this purpose, in accordance with the invention, means defining a circular, air-filled slot 12 is provided in the first embodiment illustrated in FIGS. 1 to 3 generally aligned with the separating line between the two cross-sectional regions of shaft 1 which are filled by image guide 3 and by light guide 5, respectively. This separating line extends as a projection of image guide tube 2 toward window plate 6. Slot 12 is a circular slot formed in window plate 6 inwardly from outer surface 11 substantially coaxially with the separating line, that is to say beyond the distal end of image guide tube 2. In the illustrated embodiment, the slot is rectangular in cross-section and extends about two-thirds of the way into the thickness of window plate 6.

As shown in FIG. 3, most of the light beams 10 reflected transversely in window plate 6 from light guide 5 toward the image guide beyond the end of image guide tube 2 are reflected back at the side surface of slot 12 or prevented from passing through in some other manner. The surfaces of the slot 12 can be polished for this purpose, that is to say, constructed to be highly reflective, or they can be matte to emit the light diffusely into the slot. In any event, only small amounts of stray light pass behind slot 12 into the vicinity of the image guide after multiple reflection so that the reflection disturbances are at least substantially diminished.

Figure 4:
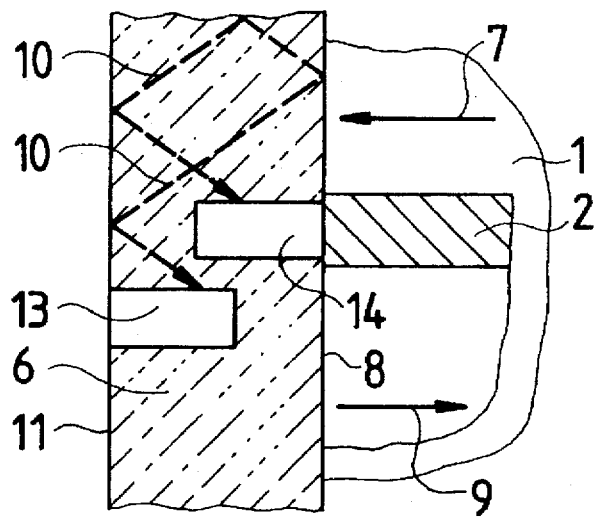
FIGS. 4–8 are sectional views, corresponding to FIG. 3, of further embodiments of window plates with different slot arrangements in accordance with the invention.

FIG. 4 is a sectional view similar to FIG. 3 of a modification in which two slots 13 and 14 are provided. These extend parallel or concentric with each other, slot 13 extending inwardly from outer surface 11 and slot 14 extending inwardly from inner surface 8 of window plate 6. Transverse reflections in the manner of dashed-line arrows 10 are prevented particularly effectively by this labyrinthine arrangement formed by laterally offset slots, which, when the slots are circular, comprise slots having different diameters.

Figure 5:
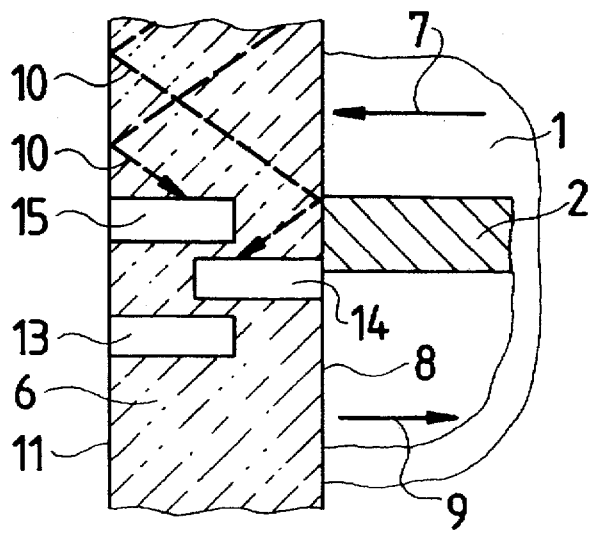

FIG. 5 shows a modification which corresponds to that of FIG. 4 but has means defining a further slot 15 extending inwardly from outer surface 11 of the window plate in addition to the slots 13 and 14 provided therein. The labyrinth effect is thereby further reinforced so that the passage of light through window plate 6 from the vicinity of the light guide into the vicinity of the image guide is nearly completely prevented.

Figure 6:
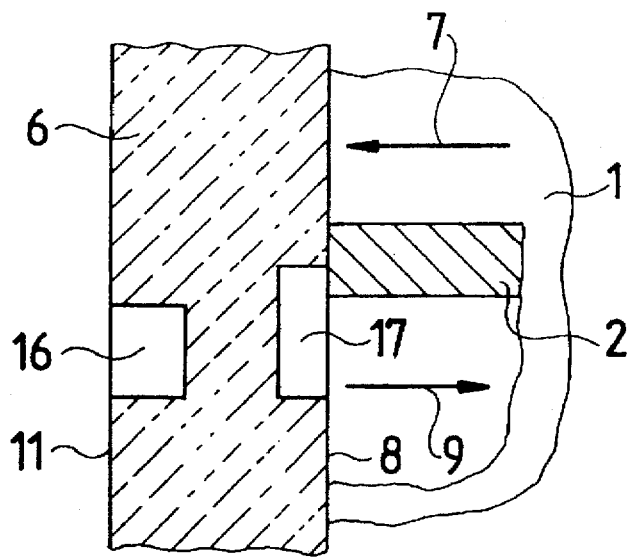

FIG. 6 shows a modification in which two flat slots 16 and 17 are provided opposite to one another, the slots being formed in outer surface 11 and inner surface 8 of the window plate 6. As shown, the slots can be of different breadths. This arrangement also results in effective reduction of the light reflections.

Figure 7:
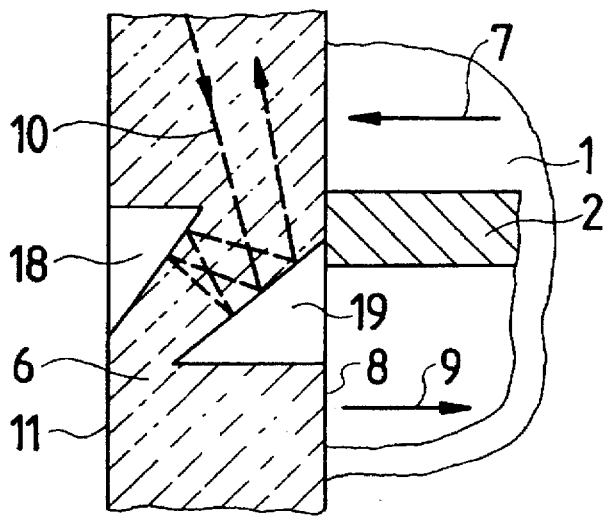

FIG. 7 shows a modification in which two oppositely disposed slots 18 and 19 are constructed with triangular cross-sections. Each slot has a wall disposed perpendicular to a surface of window plate 6 and an oblique wall. The oblique walls are arranged with respect to the principal direction of the reflected light beams to be intercepted and ensure effective labyrinthine suppression of transmitted light.

The oblique walls of the two slots can also advantageously extend obliquely to one another, as shown in FIG. 7, and define between them a light trap of the type described in D 3923007 C2.

Figure 8:
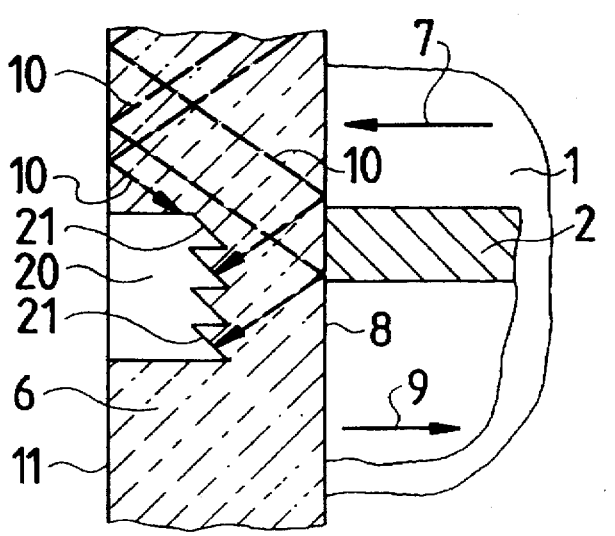

FIG. 8 shows a modification which, in a manner similar to that of the embodiments of FIGS. 1 to 3, has only one external slot 20 which is of relatively shallow construction.

Light beams reflected toward the region of the image guide can be reflected at the base of the slot which lies in a plane parallel to the surface of window plate 6. The base of the slot is therefore formed in strips with oblique surfaces 21 whose direction is so arranged that they reflect back light beams which are incident obliquely from the region of the light guide. The oblique surfaces thus lie in cones forming acute angles with surfaces 8 and 11 of the window. In an optical system having a substantially planar separation between the guides, the slot would also be straight and the oblique surfaces would lie in planes forming angles different from 0° with the inner and outer surfaces.

Further slot arrangements are possible, for instance in combination with the illustrated embodiments.

What is claimed is:

1. An endoscope optical system comprising a generally tubular shaft (1) having a distal end;

an image guide (3) in said shaft having a distal end;

a light guide (5) parallel with said image guide in said shaft and having a distal end, said image and light guides being separated from each other along a separating line; and a one-piece window mounted on said shaft at said distal ends of said image and light guides and closing said distal end of said shaft, said window having substantially parallel inner and outer surfaces, and means defining at least one air-filled slot extending into said window from at least one of said inner and outer surfaces, said at least one slot being aligned with said separating line and forming a light screen to diminish transmission of stray light from said light guide to said image guide.

2. An endoscope optical system according to claim 1 and including two air-filled slots.

3. An endoscope optical system according to claim 2 wherein one of said two slots extends into said window from said inner surface and the other of said two slots extends into said window from said outer surface.

4. An endoscope optical system according to claim 3 wherein said tubular shaft has a longitudinal axis and wherein said slots are laterally offset relative to said axis.

5. An endoscope optical system according to claim 1 wherein said at least one slot has a side wall at an angle greater than 0° from a direction normal to said inner and outer surfaces.

6. An endoscope optical system according to claim 1 wherein said at least one slot is arc-shaped in a plane parallel with said inner and outer surfaces, has side walls intersecting one of said inner and outer surfaces and a slot base between said side walls, said slot base having a surface lying in a cone at an angle greater than 0° relative to said inner and outer surfaces.

7. An endoscope optical system according to claim 1 wherein said at least one slot has side walls intersecting one of said inner and outer surfaces and a slot base between said side walls, said slot base having a plurality of surface portions each lying in a plane at an angle greater than 0° relative to said inner and outer surfaces.

* * * * *